United States Patent [19]

Benoist et al.

[11] Patent Number: 5,644,065
[45] Date of Patent: Jul. 1, 1997

[54] GENETICALLY ENGINEERED MICE CONTAINING ALTERATIONS IN THE MHC CLASS II GENES

[75] Inventors: Christophe Benoist; Diane Mathis, both of Erstein, France; Dominic Cosgrove, Omaha, Nebr.

[73] Assignees: Bristol-Myers Squibb Company, Princeton, N.J.; Institut National de la Santé et de la Recherche Médicale, Paris Cedex, France; Centre National de la Recherche Scientifique, Paris Cedex, France; Université Louis Pasteur, Strasbourg Cedex, France

[21] Appl. No.: 312,984

[22] Filed: Oct. 3, 1994

Related U.S. Application Data

[63] Continuation of Ser. No. 819,497, Jan. 10, 1992, abandoned.

[30] Foreign Application Priority Data

Jan. 10, 1991 [GB] United Kingdom .................. 9100481

[51] Int. Cl.$^6$ ..................................................... C12N 15/00
[52] U.S. Cl. ................................................. 800/2; 435/172.3
[58] Field of Search ................................................. 800/2

[56] References Cited

PUBLICATIONS

Capecchi, *TIG* 5(3):70–76 (1989).
Carbone et al., *Fundamental Immunology*, Second Edition, edited by William E. Paul, Raven Press, Ltd., New York pp. 541–567 (1989).
DeChiara et al., *Nature* 345:78–80 (1990).
Gossler et al., *Proc. Natl. Acad. Sci. USA* 83:9065–9069 (1986).
Landais et al., *J. Immunol.* 137(9):3002–3005 (1986).
Larhammar et al., *Cell* 34:179–188 (1983).
Mansour et al., *Nature* 336:348–352 (1988).
Mathis et al., *Proc. Natl. Acad. Sci. USA* 80:273–277 (1983).
Mengle–Gaw et al., *Ann. Rev. Immunol.* 3:367–396 (1985).
Nagy et al., *Immunol. Today* 10(4)132–138 (1989).
Robinson et al., *Fundamental Immunology*, Second Edition, edited by William E. Paul, Raven Press, Ltd., New York pp. 489–539 (1989).
Schwartzberg et al., *Science* 246:799–803 (1989).
Smithies et al., *Nature* 317:230–234 (1985).
Unanue, *Fundamental Immunology*, Second Edition, edited by William E. Paul, Raven Press, Ltd. New York pp. 95–115 (1989).
Zijlstra, et al., *Nature* 342:435–438 (1989).
Fehling et al., *TIG* 5(3):342–347 (1989).
Cosgrove et al *Cell* 66: 1051, 1991.
Ziglstra et al *Nature* 342:435, 1989.
Fehling et al *TIGS* 5(10): 347, 1989.
Larhammar et al. *Cell* 34: 179, 1983.
Mathis et al *PNAS* 80:277, 1983.
Lei et al *J Exp Med* 156 596, 1982.

*Primary Examiner*—Suzanne E. Ziska
*Attorney, Agent, or Firm*—Sterne, Kessler, Goldstein & Fox, P.L.L.C.

[57] ABSTRACT

The present invention provides mice which are deficient in the normal expression of one or more MHC class II genes, to mice heterozygous for such deficiency, and to cell lines, preferably pluripotent or totipotent cell lines, which are heterozygous, homozygous or chimeric for such deficiency, as well as to the use of any of the above, especially in situations where the absence of at least one MHC gene, or the normal expression thereof, is desirable.

4 Claims, 6 Drawing Sheets

GENETICALLY ENGINEERED MICE CONTAINING ALTERATIONS IN THE MHC CLASS II GENES

This application is a continuation of application Ser. No. 07/819,497, filed Jan. 10, 1992 now abandoned.

FIELD OF THE INVENTION

The present invention relates to the fields of immunology and transgenic mice. Specifically, the present invention relates to mice which are deficient in the normal expression of one or more wild-type MHC class II genes, to mice heterozygous for such deficiency, and to cell lines, preferably pluripotent or totipotent cell lines, which are heterozygous, homozygous or chimeric for such deficiency.

DESCRIPTION OF THE RELATED ART

Class II genes of the Major Histocompatibility Complex (MHC) and their products play a central role in the development and function of the immune system (Carbone, F. R., et al., "Major Histocompatibility Complex Control of T Cell Recognition," in *Fundamental Immunology*, Second Ed., ed. Williams E. P., Raven Press Ltd., New York, p. 541 (1989); Mengle-Gaw, L., et al., *Ann. Rev. Immunol.* 3:367 (1985)).

The MHC class II genes and their products are of critical importance in a number of phenomena: they control the selection of a functional T cell population of the "helper" or "inflammatory" type (CD4$^+$ T cells); and thymic selection of T cells by MHC class II molecules also leads to self-tolerance, for example. Class II gene products are the obligatory conduit for recognition of foreign antigen by helper T cells during an immune response, via "antigen presentation" (Unanue, E. R., "Macrophages, Antigen-Presenting Cells, and the Phenomena of Antigen Handling and Presentation," in *Fundamental Immunology*, Second Ed., ed. William E. P., Raven Press Ltd., New York, p. 95 (1989)).

MHC class II genes exhibit a high degree of allelic polymorphism within a species; this polymorphism leads, through restrictions at the levels of thymic selection and antigen presentation, to variation between individuals in their response to specific antigens or pathogens; this polymorphism also leads to alloreactive phenomena, such as graft rejection or graft-versus-host disease, in tissue transfers between incompatible individuals. Finally, through mechanisms which are not well understood, MHC class II genes act as predisposing genes for a number of human diseases. For example, multiple sclerosis has been found to be associated with a lesion in the HLA-DR2 gene, while diabetes has been found to be linked to HLA-DR3,4.

In more detail, the immune response of any species relies on antigen presentation by the MHCI and MHC class II (Major Histocompatibility Complex class I and II) molecules expressed by most cells. MHCI is expressed on most cells, and is primarily responsible for presenting antigens which are actually present within the cell, including self-antigens. MHC class II is mainly responsible for presenting antigens of extracellular origin and, so, is primarily responsible for presenting foreign antigens to the immune system. Expression of MHC class II is essentially limited to cells of the immune system, such as B cells, dendritic cells and phagocytes.

MHCI and MHC class II belong to the immunoglobulin superfamily, and have domains of their molecules which are closely similar to the constant (C) domains found on antibody molecules. T cell receptors (which recognize MHCI and MHC class II) also belong to this family, and possess both the variable (V) and constant regions typical of antibodies. T cells positive for CD8 (CD8$^+$) recognize, and can be activated by, antigen-presenting MHCI cells, while CD4$^+$ cells recognize, and can be activated by, antigen-presenting MHC class II cells.

The CD4 molecule is characteristically present on T lymphocyte helper cells, although it is also present on other cell types, and is known to be present in the brain. CD4 has been extensively characterized and investigated, owing to its importance in HIV infection. It is associated with the TCR, and is responsible for recognizing MHC class II (with or without antigen), serving to anchor the TCR and MHC class II molecules in close proximity, thus facilitating their interaction.

Activation of the relevant subset of T cells then leads to a proliferation of these T cells and signalling of the relevant B cells to proliferate and produce antibody against the antigen Because invading organisms can generate coat, or other, antigens which are capable of escaping the immune system, either by mimicking self antigens or the MHC class II/I molecules, or by developing structures which do not bind the MHC molecules, the MHC molecules, by way of defence, have diversified and become a polygenic family with a large number of alleles, human beings possessing several alleles for each of the MHC molecule types (of. Nagy et al., *Immunology Today* 10:132–138 (1989)).

MHC molecules, in man, form several different classes—HLA A, B or C (class I) and HLA DP, DQ or DR (class II), each class differing in the structure of its $\alpha$ or $\beta$ chain. In any one person, the exact constitution of the $\alpha$ and $\beta$ chains is inherited from the two parents.

Differences between individuals only affect those parts of the molecules allowed to vary. The other regions (responsible for binding membranes and receptors, such as CD4 and CD8), do not vary between individuals, but may vary between species. Those portions of the molecules which vary between individuals are responsible for presenting antigen to T cells. Thus, any two individuals will usually respond in different ways to any given antigen.

Because they present the antigen, the MHC molecules also determine which T cell receptors (TCRs) will react with them, a function which is dependent on the variable regions of the TCR $\alpha$ and $\beta$ chains, $V_\alpha$ and $V_\beta$. As there is no selection pressure on TCRs not to recognize foreign MHC, there are large numbers of cells in any individual which can, and will, recognize the variable regions of another individual's MHC.

TCRs recognizing the individual's own MHC will not do so unless a foreign antigen is presented by the antigen-presenting cleft (MHC cell restriction). The TCR recognizes the shape of the MHC surface. For reasons which are not fully understood, foreign MHC is seen as self MHC presenting a foreign antigen by many T cells.

Thus, problems arise on introduction of foreign immunocompetent cells, with many populations of T cells becoming activated and proliferating, ultimately leading to Graft versus Host disease (GVHD).

GVHD is characterized by: massive proliferation of certain blood cells associated with the immune system; loss of immune responsiveness and self tolerance; and other conditions, such as thymus degeneration and splenomegaly.

The incoming T cells recognize the host's MHC molecules as self MHC presenting foreign antigen, and react accordingly. The host's cells are attacked through inflammatory processes and direct cytotoxicity, without being specifically directed to any pathogens. Such a reaction can ultimately lead to the death of the recipient.

One unresolved puzzle, for example, is why can a productive infection of HIV can be generated in the chimpanzee, without the chimpanzee developing any of the symptoms of AIDS? Characterization of MHC of the chimpanzee demonstrates that chimpanzee MHC differs by only a few amino acids from human MHC and, yet, the chimpanzee apparently remains perfectly healthy. This and other problems may be solved by being able to make use of a system where the MHC class II present was dictated by the skilled person, rather than the system.

Mice are the models of preference in the study of the mammalian genetic system, and a great deal of research has been performed to map the murine genome. It was study on the mouse which first led to the discovery of the major histocompatibility complex.

Most mice have two protein complexes encoded by MHC class II genes: the A and E complexes. Each is composed of an α and β chain (thus $A_\alpha A_\beta$ and $E_\alpha E_\beta$, Robinson, M. A., et al, "Major Histocompatibility Complex Antigens and Genes," in *Fundamental Immunology*, Second Ed., ed. William E. P., Raven Press Ltd., New York, p. 489 (1989)). However, some mice do not possess a functional E complex, because of genetic lesions in the E α gene (such as the C57B1/6 or 129 mouse strains; Mathis, D. J., et al., *Proc. Natl. Acad. Sci. USA* 80:273 (1983)).

Thus, it would be of great importance to be able to establish a living model wherein the role of MHC class II could be studied in a definitive manner.

Accordingly, it is an object of the present invention to generate strains of mice devoid of MHC class II genes. Such mice would be of great value for a better understanding of the role of class II genes, and also allow direct testing of the function of specific genes reintroduceable by transgenesis, without interference from endogenous class II genes.

SUMMARY OF THE INVENTION

The present invention provides mice and mouse cell lines which are deficient in the normal expression of the major histocompatibility class II A complex. Specifically, the present invention describes mice which have been genetically altered such that the normal expression of the MHC class II A locus has been modified.

The invention further provides mice and cell lines which are heterozygous for the above deficiency.

Utilizing the above described mice and cell lines, a method of identifying the MHC class II protein bound by an antigen is provided. Specifically, the class of MHC bound by an antigen can be identified by first incubating an antigen with a cell line (a) which displays normal MHC class II gene expression, second, incubating an antigen with a cell line (b) which is deficient in the normal expression of 1 or more of the MHC class II alleles, and third, determining the amount antigen bound by (b) relative to the amount bound by (a).

DESCRIPTION OF THE PREFERRED EMBODIMENTS

The present invention provides mice which are deficient in the normal expression of one or more MHC class II genes, mice heterozygous for such deficiency, and cell lines, preferably pluripotent or totipotent cell lines, which are heterozygous, homozygous or chimeric for such deficiency, as well as to the use of any of the above, especially in situations where the absence of at least one MHC gene, or the normal expression thereof, is desirable.

In a first aspect, the present invention provides a mouse deficient in the normal expression of at least the major histocompatibility class II A complex.

It will be appreciated that such mice may be heterozygous or homozygous for the desired trait, provided that the mice are deficient as defined.

In an alternative aspect, the present invention provides mice not showing the deficiency, but which are heterozygous for said deficiency, and cell lines, preferably pluripotent or totipotent cell lines, which are heterozygous, homozygous or chimeric for said deficiency.

Any suitable mouse may provide the basis for a mouse of the invention, although it will be appreciated that mice already lacking in one MHC class II gene product will be preferred. Many suitable mice are known and available, such as those of strain 129, deficient in the expression of the E complex.

By "deficient" is meant is meant lacking, or substantially completely lacking, in normal expression. It will be understood that, where the gene is lacking, no expression will be possible. However, where the relevant gene is mutated by, for example, an insertion event, it may be possible for extremely low quantities of product to be produced, although such product may, in itself, be inoperative, or not subject to the usual physiological actions (expression on the cell surface, for example).

With regard to "normal expression," this refers to a level of expression which is a significant proportion of that which would be expected in a wild-type animal. In an animal of the invention, a product of some sort may possibly be expressed, but will either not be operative, or will only be expressed in insignificant levels insufficient to support normal MHC class II function.

Lack of, or abnormal expression of, one MHC class II gene product will render the relevant complex inoperative, or prevent formation of the complex altogether, thus making it unnecessary, although envisaged by the invention, to affect more than one gene. For example, it will generally be sufficient to rotate just the $A_\beta$ gene or the $A_\alpha$ gene to prevent any of the A complex being expressed.

As indicated, it is highly desirable that there be either no, or no appreciable, expression of any MHC class II complex. This is generally best achieved by use of a mouse type deficient in the E complex (however this may occur). It is possible to mutate a mouse strain to eliminate expression of both E and A complexes but, for ease of production, a known mouse already lacking the E complex is preferable for the starting material.

In the preferred mice, wherein there is no expression of either the A or B complexes, there may be a certain amount of extremely limited expression of a hybrid MHC complex comprising, for example, the $A_\alpha$ and $E_\beta$ sub-units, although such a complex has not been observed. In addition, such a complex would probably have react differently with the TCR, if it reacted at all.

The mice of the invention are deficient in the expression of the A complex of MHCII to the extent that any function dependent on the presence of the A complex can be properly performed, if at all. Thus, for example, the population of $CD4^+$ T cells, which specifically recognize MHCII, may well be severely affected by the absence of the A complex. This is the case when both the A and E complexes are absent, and the absence of only the A complex can establish whether the E complex serves any unique purpose, or whether the E complex is sufficient in itself to support normal MHCII function.

The absence of any MHC class II product can also allow investigation into the possibility of restoring the $CD4^+$ T cell population by other means, such as by using foreign genes, or by the introduction of a drug or other heterologous product.

Such a system also allows the investigation of a whole, in vivo, system lacking only the MHC class II associated aspect of the immune network, and will allow researchers to establish the importance of other, relatively minor, constituents, whose effects could not previously have been determined because of the dominant effect of MHCII.

MHCII deficient mice in accordance with the invention can also be used to investigate the introduction of foreign genes without any problems associated with immune rejection. GVHD can be investigated without the complication of catering for the host's response, and immune deficient conditions can be investigated prophylactically, symptomatically or by having the actual causative agent present. Such investigations may be particularly important in the investigation of treatments for AIDS, for example.

The mice of the invention may also be deficient in the expression of other genes, and this provides a further aspect of the invention. Such mice can be used to investigate other components of the immune system, for example.

Treatments for various diseases can be examined without the complicating presence of an immune response, and without the Jerne idiotype/antiidiotype network, so that passive vaccines may be tested and fully evaluated.

Also, as described above, abnormal human MHC genes may act as predisposing agents towards various diseases, and the mice of the invention can be used to study the affect of introducing lesions into human MHC in a non-human, whole organism environment. Thus, not only can the symptoms and morphology of such diseases be studied, but potential treatments can be assayed. This forms a preferred feature of the present invention.

Mice of the invention may be obtained by the method known as homologous recombination (HR). This method has long been known in prokaryotic species, and has recently been described for the mouse (for review, see TIG 5(3):70–76 (1989)).

Homologous recombination essentially comprises isolating the target gene, employing known genetic engineering techniques to mutate or otherwise disable or modify the gene, and then reintroducing the gene into the relevant species. This is achieved by preparing a culture of pluripotent, or totipotent, cells, typically taken from embryos. The advantage of these cells is that they can be successfully cultured for a large number of generations under conditions in which they will not differentiate.

Typically by the technique of electroportation, the cells, such as embryo stem (ES) cells, are rendered capable of taking up exogenous DNA. The modified gene is then introduced, in a suitable manner, to these cells. Once taken up, recombination may occur, although this may be by insertion as well as by homologous recombination.

To select cells in which the desired recombination event has taken place, a marker may be used. For example, it is well known to employ a bacterial Neogene to confer resistance to neomycin, or an analogue thereof, such as G418. The marker gene may be inserted in the gene to be modified, thereby disabling the target gene, while providing a marker. Clones which are $Neo^+$ have undergone recombination.

To further select homologous recombinants, the ends of the modified gene may have other markers tagged on, such as the Herpes Simplex Virus thymidine kinase (HSVTK) gene. In a HR event, the HSVTK genes will not be recombined, and the marker will not be transferred. Therefore, desired recombinants will be resistant to, for example, Gancyclovir, which is converted into a toxic metabolite when the HSVTK gene product is present (after a non-homologous recombination event). Information necessary to enable the skilled person to isolate the required genes is described, for example, by McKnight, S. L., *Nucl. Acids Res.* 8:5949 (1980).

Correct clones may also be identified by the somewhat more laborious technique of PCR, when the structure of the mutated gene is known. However, this technique is essentially no longer used.

Subsequently, when a suitable clone has been identified, the ES cells may be injected into early-stage embryos, or blastocysts, and reintroduced into a pseudopregnant female.

Chimeric animals will generally result from at least some of these embryos, their tissues deriving in part from the selected clone. Thus, the germ-line will also be chimeric, spermatozoa or ova containing the selected gene. Progeny deriving from such germ cells will be heterozygous for the gene.

The heterozygous progeny can be cross-bred to yield homozygous animals. Confirmation of the allelic structure of the mice can be ascertained by Southern blotting, for example.

The present invention also envisages cell lines suitable for generating mice of the invention, and techniques for generating such lines and the mice.

Thus, to obtain mice according to the present invention, we followed the strategy of homologous recombination (HR) in embryonic stem cells (ES cells) to destroy the $A_\beta$ gene, a strategy pioneered by the work of Smithies and Cappecchi (Smithies, O., et al., Nature 317:230 (1985); Zijlstra, M., et al., Nature 342: 435 (1989); Schwartzberg, P. L., et al., Science 246:799 (1989); DeChiara, T. M., et al., Nature 345:78 (1990)).

Using recombinant DNA technology, an altered $A_\beta$ gene was constructed. This gene was effectively destroyed by insertion of exogenous DNA sequences into the region coding for the first domain of the mature protein, and is hereinafter referred to as $A_\beta^o$.

This DNA was then introduced by electroportation into toilpotent embryonic stem cells derived from mouse strain 129. Clones of transformed cells were selected in which the altered $A_\beta$ gene had replaced, by homologous recombination, its normal counterpart. These cells were then used to obtain chimeric mice which, on breeding, could pass on the $A_\beta^o$-containing chromosome to subsequent generations of mice as a classical genetic trait.

The recombinant DNA used to disrupt the $A_\beta$ gene was constructed in two steps. The first step involved insertion of a bacterial gene, encoding a neomycin resistance marker, into the structural $A_\beta$ gene to physically inhibit the function of the gene, while also providing a means of selecting cells that have stably incorporated the construct into their genomic DNA.

The second part of the construction was designed to place Herpes Simplex Virus thymidine kinase (HSVTK) genes at both ends of the modified $A_\beta$ gene. As originally described by Mansour (Mansour, S. L., et al., Nature 336:348 (1988)), this construction provides a selectable marker against non-homologous recombination events, since these sequences will be deleted in a HR event, but not in a non-homologous recombination event. The HSVTK gene product acts by converting nucleoside analogues, such as gancyclovir, into toxic metabolites, allowing selection for the loss of the HSVTK segments.

ES cells were then subject to electroportation and introduced to the linearized DNA, either with or without HSVTK genes. The cells were selected according to their markers and then used to inject into morulae. Pseudopregnant mice were then impregnated, and the heterozygous offspring cross-bred until homozygous $A_\beta^{o/o}$ mice were obtained.

Populations of CD4$^+$ T cells are severely affected by the lack of any MHC class II expression (this population is "educated" by and recognizes antigens in the context of MHC class II molecules). Thus, $A_\beta^{o/o}$ mice, devoid of MHC class II gene products, will permit experiments to be performed which otherwise would be valueless in the presence of a naturally occurring MHC class II gene product. For example, it will be possible to: reintroduce normal genes to evaluate directly their impact on the T lymphocyte repertoire; to observe responses to specific antigens (peptides, proteins, bacteria, viruses); and to investigate autoimmunity. Reintroduced class II genes could originate from species other than mouse (e.g. human, bovine). Functional dissection of class II genes can also be undertaken in such a system, using naturally occurring or in vitro generated mutants.

The $A_\beta^{o/o}$ mice should be extremely immunodeficient, as they are essentially lacking helper T cells. The virtually abolished CD4$^+$ population, the drastically altered CD4/CD8 ratio, and immunodeficiency constitute a phenotype similar to that seen in advanced cases of AIDS. The absence of class II expression is even more related to human SCID patients, in which severe immunodeficiency is due to a genetic defect in MHC class II regulatory factors. The $A_\beta^{o/o}$ mice may, thus, be very useful in investigating opportunistic infections and possible therapeutic action in such immunocompromised hosts.

Thus, it will be appreciated that there are many uses to which the mice of the invention may be put. They are particularly useful in studying any aspect of the immune system having to do with MHC class II, such as the nature of the molecule, wherein experiments may involve mutated MHC class II to investigate the effect of structure, or to establish how different the structure must be to elicit an immune response. Also, as stated, the mice may be used as drug or passive vaccine models, a particularly preferred feature of the invention.

The following Examples serve only to illustrate the invention, and are not to be construed as in any way limiting on the invention.

EXAMPLE 1

Preparation of Plasmid Containing a Mutant $A_\beta$ Gene

A. Preparing the $A_\beta$ Gene containing Neo

The recombinant DNA used to disrupt the $A_\beta$ gene was constructed in two steps. The first step involved insertion of the neomycin resistance marker into the structural $A_\beta$ gene.

Figure 1A:
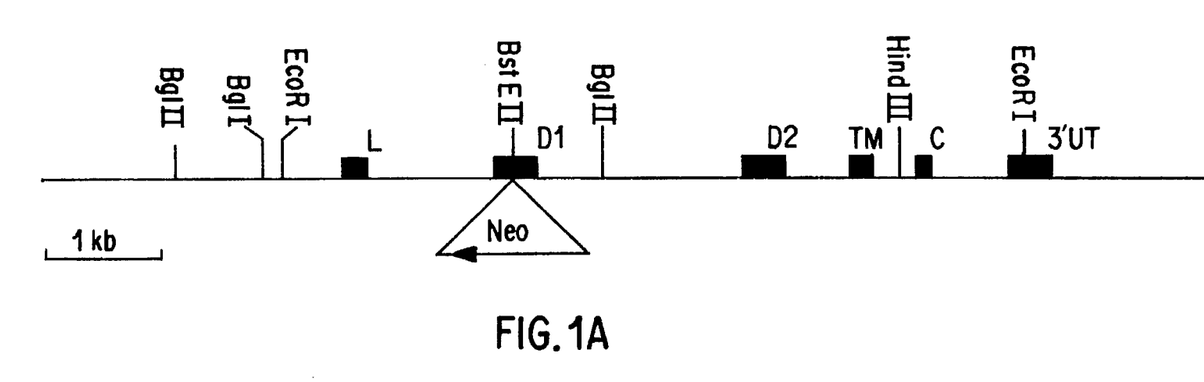
FIG. 1A shows a restriction map of the MHC class II $A_\beta$ gene. The black boxes correspond to the gene's exons (1, D1, D2, TM, C and 3' UT denote the leader, 1st domain, 2nd domain, transmembrane, cytoplasmic and 3' untranslated exons, respectively).

The starting material was a 6.3 kb fragment of the $A_\beta$ gene, present in the plasmid pEXV-3 (obtained from Dr. R. Germain, NIH). The sequence of this segment is known (cf. Larhammar, D., et al., Cell 34:179 (1983)). The unique BstEII restriction endonuclease recognition sequence located in the second exon was used as the site for insertion (FIG. 1A).

The gene conferring resistance to neomycin-like drugs was introduced into the unique BstEII site in the second exon.

The neomycin resistance gene used was the 1.1 kb XhoI/HindIII fragment from the pMC1Neo PolyA plasmid (Stratagene, Inc. ). This fragment was introduced into the BstEII site of the $A_\beta^b$-containing plasmid by standard recombinant DNA technology. This altered gene will hereafter be referred to as $AO_\beta$.

B. Preparation of Electroporation Plasmid

Figure 1B:
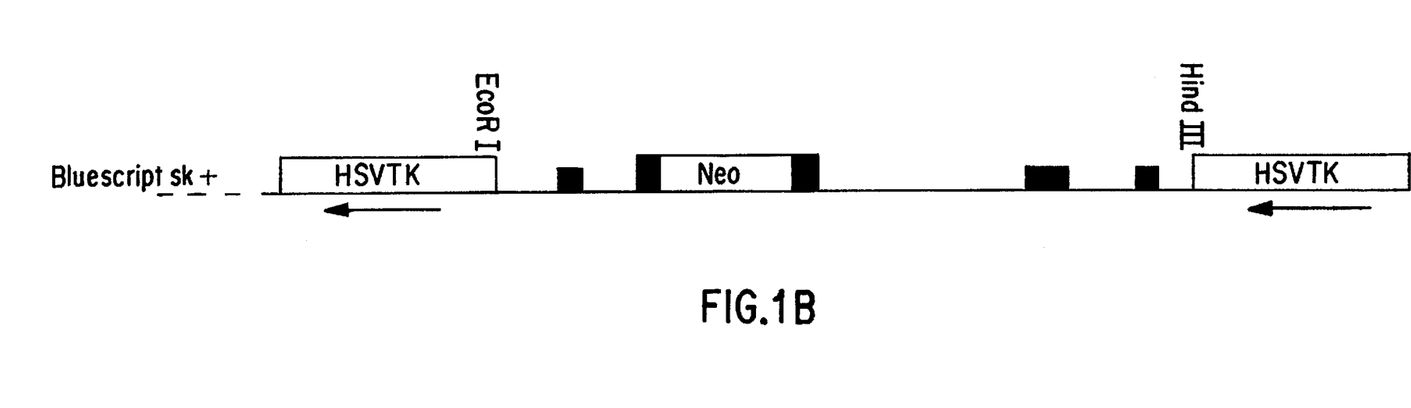
FIG. 1B shows the above described DNA construct for electroporation of ES cells. The schematic illustrates the 5.5 kb EcoRI-HindIII fragment of genomic DNA containing the 1.1 kb neomycin resistance marker and flanked by two 1.8 kb HSVTK genes. The Bluescript SK$^+$ plasmid sequences were left on the construct. The arrows denote the direction of transcription of the genes encoding selectable markers.

Herpes Simplex Virus thymidine kinase (HSVTK-c.f. McKnight, supra) genes were then inserted at both ends of the modified $A_\beta$ gene. First, a recombinant plasmid was created, carrying two copies of the HSVTK gene, prepared by SalI cleavage, and cloned in a head-to-tail configuration in the SalI site of pBluescript, thereby generating a new SalI site between the two HSVTK copies. Into this site was cloned the EcoRI-HindIII fragment from the $A_\beta$ gene, cleaved from the pEXV-3 plasmid carrying the insertion, resulting in the plasmid shown in FIG. 1B.

EXAMPLE 2

Electroporation and Selection of Toilpotent Embryonic Stem Cells

A. Electroporation

The D3 embryonic stem cell line (derived from a mouse of the 129 strain) was provided by Dr. Roll Kemmler (Gossler, A., et al., Proc. Natl. Acad. Sci. USA 83:9065 (1986)). The cells were frozen stocks from the 14th passage, and were maintained in Dulbecco's Modified Eagle Medium (DMEM), supplemented with 10% foetal calf serum (FCS), 0.06% L-glutamine, 1000 u/ml leukaemia inhibitory factor (LIF-available from AMRAD Ltd., 1727 Coltham Rd., Kew, Victoria 3101, Australia, under the trade mark "ESGRO"), and 500 μg/ml gentamycin sulphate. Cells were carried on gelatinized plates in a 37° C. incubator gassed with 10% $CO_2$, and passaged by trypsinization with a Hanks balanced salts solution supplemented with 0.25% trypsin, 0.04% EDTA.

The plasmid made in Example 1B (FIG. 1B) was linearized with NotI (cleaving in the pBluescript polylinker) and purified by phenol/chloroform extraction and ethanol precipitation.

To perform the electroporation, $1-2 \times 10^7$ D3 cells were resuspended in 500 μl of DMEM with 15% FCS, and shocked with a BioRad Gene Pulser equipped with a capacitance extender set at 1000 V/cm and 12.5 μF, in the presence of 5 μg of linearized DNA; after five minutes, the cells were diluted and plated at $2 \times 10^6$ cells/cm plate. Cells were electroporated with either the linearized plasmid from Example 1B, or the 5.5 kb EcoRI-HindIII fragment of genomic DNA containing the 1.1 kb neomycin resistance marker, from Example 1A.

B. Selection

Figure 1C:
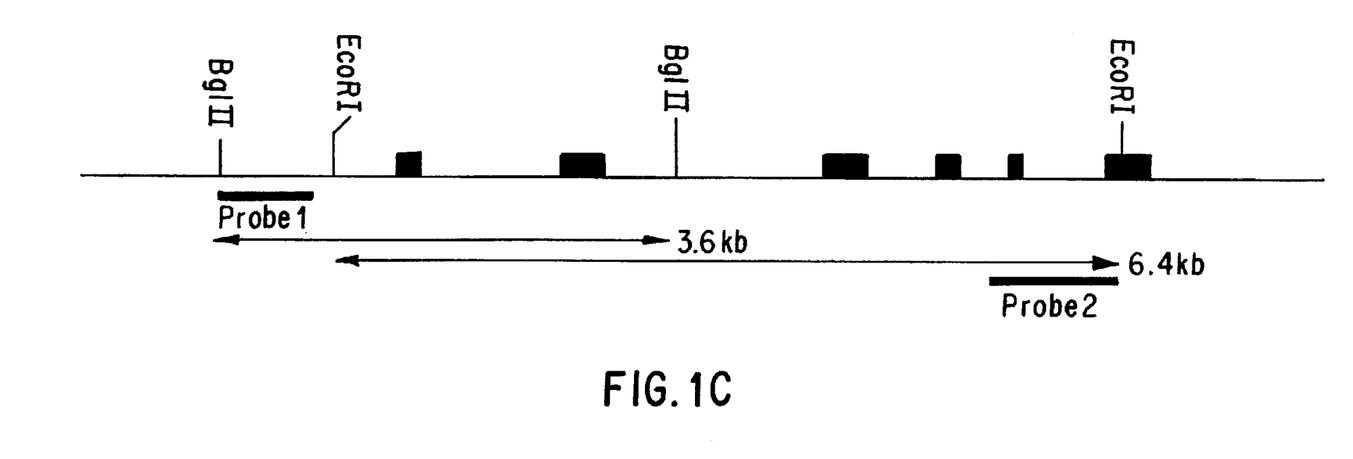
FIGS. 1C and 1D show verification of homologous recombination in ES cells by Southern blot analysis of genomic DNA. The schematics show the fragments obtained from wild-type $A_\beta$ (C), or $A_\beta^o$ (D), after digestion with EcoRI and hybridization with probe #2.
Figure 1D:
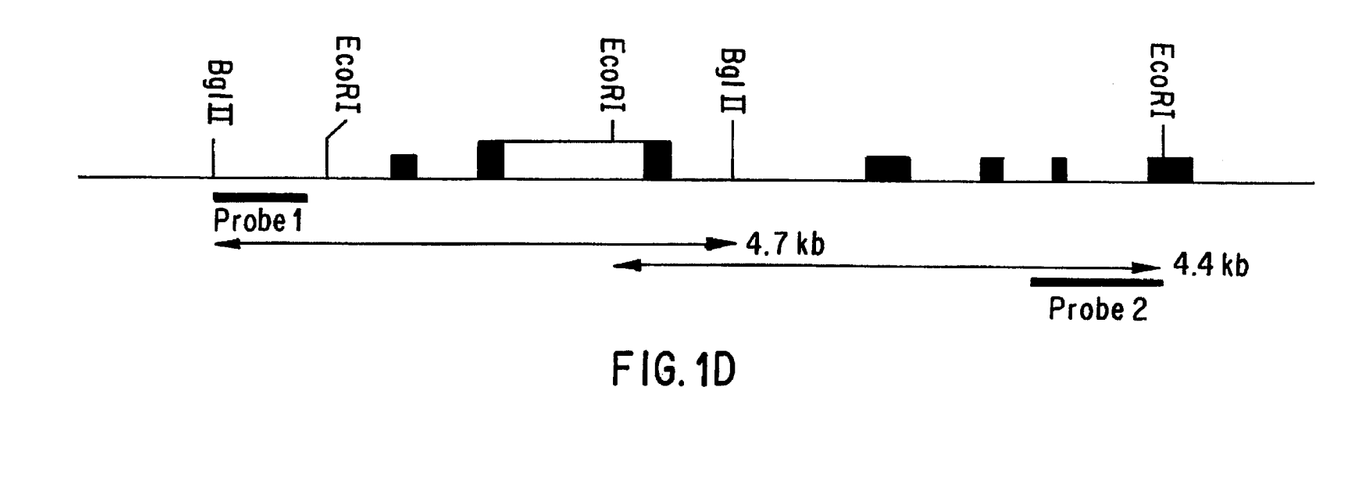

After 12 hours, the medium was changed and supplemented with 150 μg/ml G418 (available from Gibco BRL, Cengy-Pontoise, France) and 2 mM gancyclovir (available from Boehringer-Mannheim, D-6800 Mannheim, Germany). The medium was changed every three days throughout the 16 day selection period. Resistant colonies were harvested by scraping and aspirating into a sterile drawn microcapillary and transferred onto fibroblast feeder layers on a 48-well plate. Clones were monitored daily and sequentially transferred into 24-well plates, then into successive petri dishes of 3, 6, and 10 cm diameter. An aliquot of each clone was frozen and DNA prepared from the remainder. It was digested with EcoRI, and analyzed by Southern Blot for homologous recombination using probe #2 (FIGS. 1C, D).

Any homologous recombination event should lead to the replacement of the normal 6.4 kb band by a shorter 4.4 kb band. HR events which indicated as successful by this method were then confirmed by another Southern blot (a BglII digest, probed with probe #1). Of 175 clones analyzed, 4 corresponded to HR events.

Clones transfected with the $A_\beta^o$ gene and containing the Neo insert, but lacking the HSVTK genes, were selected with G418 alone. Approximately twice the number of resistant clones were obtained compared with the double selection experiments. Of 42 such clones analyzed, by Southern blots, 1 corresponded to an HR event.

Figure 1E:
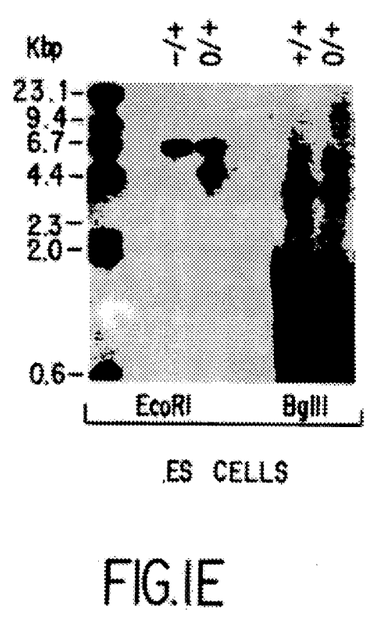
FIG. 1E shows identification of KR events in ES cells. Examples are shown of a normal clone (+/+) and of a done carrying a homologously recombined $A_\beta^o$ gene (+/0), with digestion by EcoRI (probe #2) and BglII (probe #1). Interpretation is as provided with regard to FIGS. 1C and D above.

FIG. 1E shows identification of KR events in ES cells. Examples are shown of a normal clone (+/+) and of a clone carrying a homologously recombined $A_\beta^o$ gene (+/0), with digestion by EcoRI (probe #2) and BglII (probe #1). Interpretation is as provided with regard to FIGS. 1C and D above.

EXAMPLE 3

Generation of Transgenic Mice

A. ES Cell/Morulae Conjugates

Of the various clones generated, clone #138 was selected for further experimentation. The ES line containing clone #138 has been deposited under the designation $D3/A_\beta^o/138$ at the European Collection of Animal Cell Cultures, Porton Down, Salisbury, Wiltshire SP4 0JG, United Kingdom, in accordance with the terms of the Budapest Treaty, and bearing Accession No. 91010908 on 9th Jan. 1991.

All manipulations were performed as described by E. J. Robertson (Robertson, E. J., *Teratocarcinomas and Embryonic Stem Cells:A Practical Approach*, Ed. E. J. Robertson, IRL Press Limited, British Library Cataloguing in Publication Data (1987)). Essentially, the blastocysts were obtained from superovulated C57B1/6 female mice, at day 3.5 of pregnancy. Mature blastocysts were collected into a microcapillary and transferred into a fresh petri dish. Morulae were collected and cultured for 4 hours at 37° C. to allow blastocyst formation. Between 8 and 12 ES cells (clone #138) were injected into the blastocoel cavity of mature blastocysts. Successfully injected blastocysts were placed in culture (37° C., 5% ($CO_2$) for 3 hours to allow reparation of the membrane prior to reimplantation.

B. Transgenic Mice

Blastocysts were surgically reimplanted into the uteri of pseudo-pregnant C57B1/6×SJL female mice. Chimeric offspring were scored by coat color (streaks of 129-derived agouti hair on the black C57B1/6 hair).

Chimeric male mice were crossed with C57B1/6 females, and the offspring scored for transmission of the embryonic stem cell genotype to the germ line, on the basis of coat color (agouti coat color being indicative of germ line transmission).

Transmission of the $A_\beta$ gene to the agouti offspring was confirmed by Southern blot analysis of EcoRI-digested DNA isolated from tail biopsies hybridized with probe 2 (FIGS. 1C, D). Heterozygous offspring ($A_\beta^{o/+}$) were crossed with each other to produce $A_\beta^{o/o}$ homozygous mice.

Figure 1F:
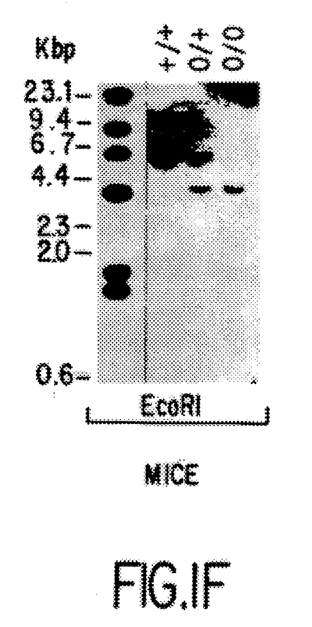
FIG. 1F shows Mendelian transmission of the $A_\beta^o$ trait. Two $A_\beta^{+/o}$ animals, progeny from the original chimeric mouse, were mated. Tail DNA from some of their offspring was analyzed by Southern blot, showing the segregation of wild-type (+) or altered (o) $A_\beta$ genes.

FIG. 1F shows Mendelian transmission of the $A_\beta^o$ trait. Two $A_\beta^{+/o}$ animals, progeny from the original chimeric mouse, were mated. Tail DNA from some of their offspring was analyzed by Southern blot, showing the segregation of wild-type (+) or altered (o) $A_\beta$ genes.

EXAMPLE 4

Confirmation of $A_\beta^{o/o}$ Status of Mice

Homozygous $A_\beta^{o/o}$ animals possess non-functional $A_\beta$ genes on both chromosomes. To verify this, the mice were tested for expression of MHC class II genes in lymphoid organs.

A. Cytofluorimetric Analysis

Figure 2A:
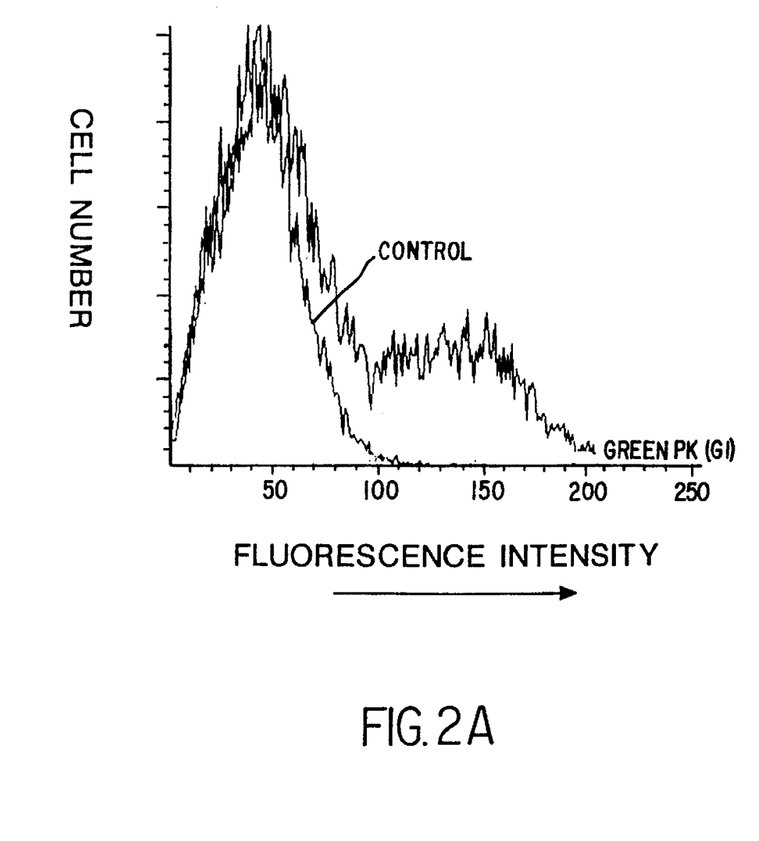
FIGS. 2A (control) and 2B ($A_\beta^{o/o}$) shows cytofluorimetric analysis of B lymphocytes from spleen and lymph nodes with several anti-class II monoclonal antibodies (such as BP 107.2.2, with ATCC Accession Number TIB 154); c.f. Landais, D., et al., *J. Immunol.* 137:3002 (1986)).
Figure 2B:
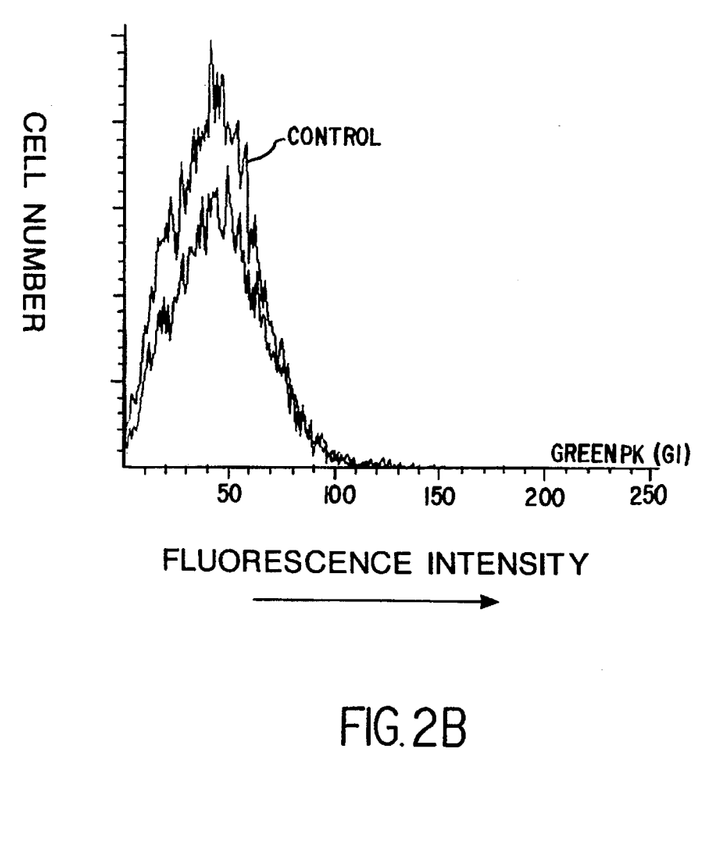

Cytofluorimetric analysis was performed on B lymphocytes from spleen and lymph nodes with several anti-class II monoclonal antibodies (such as BP 107.2.2, with ATCC Accession Number TIB 154); e.f. Landais, D., et al., *J. Immunol.* 137:3002 (1986)). Results are shown in FIG. 2. As is clearly demonstrated by the example shown in FIG. 2, no detectable $A_\beta$ protein is present on the cell surface in the $A_\beta^{o/o}$ mice.

B. Immunofluorescence

Figure 3A:
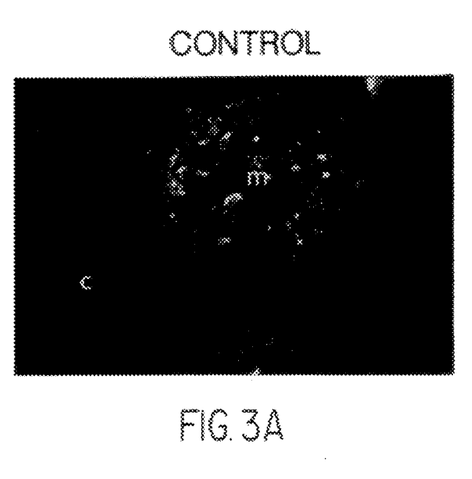
FIGS. 3A (control) and 3B ($A_\beta^{o/o}$) shows immunofluorescence staining of thymus thin sections with class II specific antibodies.
Figure 3B:
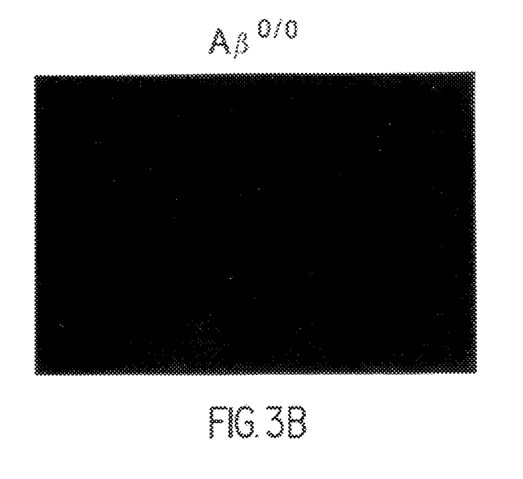

Class II expression was also investigated by immunofluorescence in cryostat sections of lymphoid organs in $A_\beta^{o/o}$ and control mice (thymus, spleen, lymph nodes). Whereas A-complex staining was readily detectable in the thymus from a control mouse, no fluorescence was seen with thymus from the $A_\beta$ mouse. Results are shown in FIG. 3.

Cryostat sections of thymuses from $A_\beta^{+/+}$ (A), or $A_\beta^{o/o}$ (B), mice were stained with an FITC-conjugated monoclonal antibody specific for the $A_\alpha$ chain. The slides were visualized by fluorescence microscopy (FIG. 3). Strong MHC class II staining was observed in the thymic medulla of the normal mouse (m), and fainter staining in the cortex (c). No staining was detected in sections from the $A_\beta^{o/o}$ mouse.

EXAMPLE 5

Effects on the Immune System

To test whether the population of CD4$^+$ T cells was affected, a fluorescence-activated cell sorting analysis was performed on each of a normal mouse and an $A_\beta^{o/o}$ mouse.

$2\times10^5$ lymph node cells were stained with FITC-conjugated anti-CD8 and phycoerythrin-conjugated anti-CD4. The stained cells were analyzed on an ATC 3000 cytofluorimeter (FIG. 4).

Figure 4A:
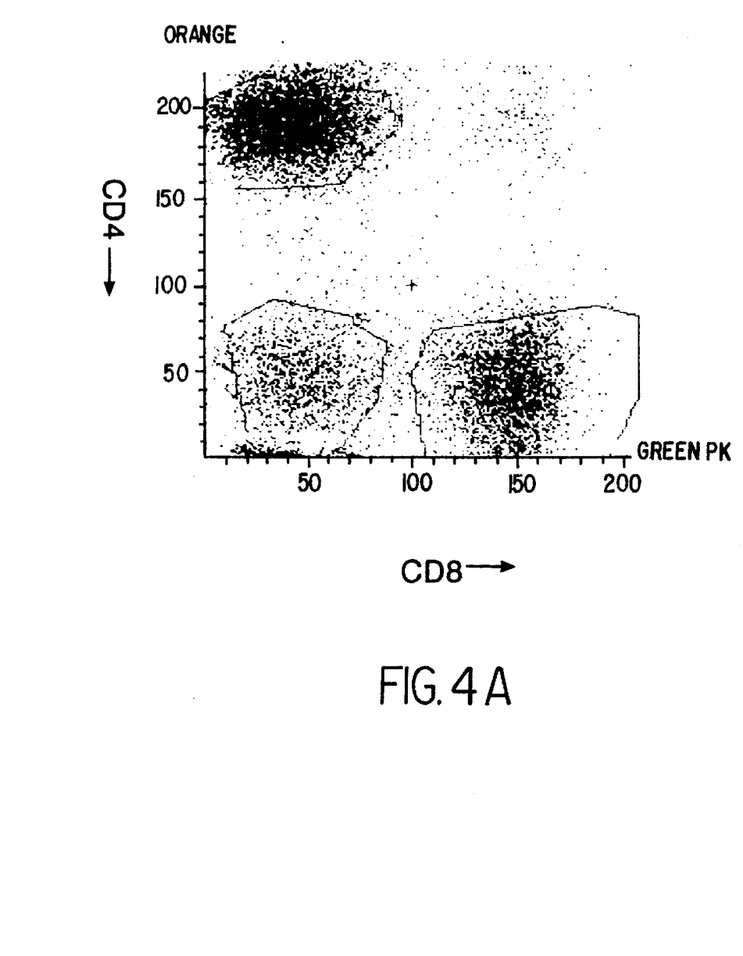
FIGS. 4A (control) and 4B ($A_\beta^{o/o}$) shows a FACS profile of CD4- and CD8-expressing cells in the lymph node of a normal littermate (FIG. 4a) and an $A_\beta^{o/o}$ mouse (FIG. 4B).

FIG. 4A shows the profile of the normal littermate. The expected pattern of strong staining of both CD4$^+$ and CD8$^+$ populations is seen.

Figure 4B:
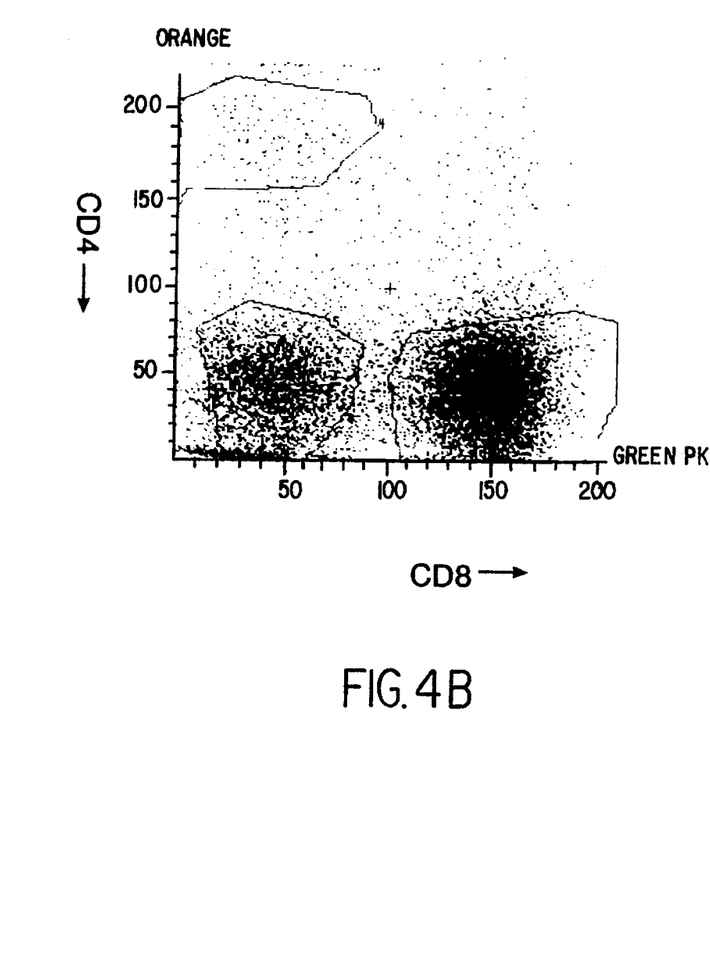

FIG. 4B shows the profile of an $A_\beta^{o/o}$ mouse. A near complete absence of CD4$^+$ cells is seen.

As expected, CD4$^+$ T cells formed a major subpopulation in the lymph node of the control mouse (FIG. 4A). By contrast, they were virtually absent from the $A_\beta^{o/o}$ animal (in relative terms, a 98% reduction in the frequency of CD4$^+$ cells is seen). The CD4 to CD8 ratio, normally around 2, was reduced to 0.05.

What is claimed is:

1. A mouse whose somatic and germ line cells contain an inserted exogenous DNA sequence in an exon of the major histocompatibility class IIAβ gene locus such that the insertion prevents functional Aβ chain protein from being expressed and wherein lack of functional Aβ chain protein prevents expression of functional major histocompatibility II AαAβ complex by cells of said mouse.

2. The mouse of claim 1, wherein said exogenous DNA is a selectable marker gene.

3. The mouse of claim 1, wherein said exon is the D1 exon.

4. The mouse of claim 1, wherein said mouse further contains an endogenous mutation which prevents the expression of functional MHC class II E-complex.

* * * * *